United States Patent [19]

Holton

[11] Patent Number: 5,717,115

[45] Date of Patent: Feb. 10, 1998

[54] METAL ALKOXIDES AND AMMONIUM ALKOXIDES

[75] Inventor: Robert A. Holton, Tallahassee, Fla.

[73] Assignee: Florida State University, Tallahassee, Fla.

[21] Appl. No.: 476,357

[22] Filed: Jun. 7, 1995

Related U.S. Application Data

[63] Continuation-in-part of Ser. No. 862,778, Apr. 3, 1992, Pat. No. 5,229,526, and a division of Ser. No. 34,247, Mar. 22, 1993, Pat. No. 5,430,160, which is a continuation-in-part of Ser. No. 949,107, Sep. 22, 1992, abandoned, which is a continuation-in-part of Ser. No. 863,849, Apr. 19, 1992, abandoned, which is a continuation-in-part of Ser. No. 862,955, Apr. 3, 1992, abandoned, which is a continuation-in-part of Ser. No. 763,805, Sep. 23, 1991, abandoned, said Ser. No. 862,778, is a continuation-in-part of Ser. No. 763,805.

[51] Int. Cl.$^6$ ............................................ C07D 305/14
[52] U.S. Cl. ............................................ 549/510; 549/511
[58] Field of Search ............................... 549/510, 511

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,924,012 | 5/1990 | Colin et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |
| 5,136,060 | 8/1992 | Holton | 549/510 |
| 5,175,315 | 12/1992 | Holton | 549/510 |
| 5,229,526 | 7/1993 | Holton | 549/213 |
| 5,274,124 | 12/1993 | Holton | 549/214 |
| 5,430,160 | 7/1995 | Holton | 549/510 |

FOREIGN PATENT DOCUMENTS

| | | |
|---|---|---|
| 0 247 378 | 4/1986 | European Pat. Off. . |
| 0 253 738 | 7/1986 | European Pat. Off. . |
| 0 253 739 | 7/1986 | European Pat. Off. . |
| 0 336 840 | 4/1988 | European Pat. Off. . |
| 0 336 841 | 4/1988 | European Pat. Off. . |
| WO 92/09589 | 11/1991 | WIPO . |

OTHER PUBLICATIONS

W.R. Chan, et al. "Tax–4(16), 11–diene–5α, 9α, 10β, 13α–tetraol, a New Taxane Derivative from the Heartwood of Yew (T. baccata L.) :X–Ray Analysis of a p–Bromobenzoate Derivative" Chem. Commun. 923 (1966).

Della Casa De Marcano, et al. "The Isolation of Seven New Taxane Derivatives from the Heartwood of Yew (Taxus baccata L.)" Chem. Commun. 1282 (1969).

Ettouati, L., et al. "Plantes de Nouvelle–Calédonie. 114. Taxanes isolés des feuilles d'Austrotaxus spicata Compton (Taxacées)" Bull. Soc. Chim. France 749 (1988).

Kingston, D.G.I., et al. "The Taxane Diterpenoids," Progress in the Chemistry of Organic Natural Products, Wein, N.Y., Springer–Verlag, 1993.

Kingston, D.G.I., et al. "New Taxanes from Taxus Brevifolia" J. Nat Prod. 45, 466 (1982).

Liu, C.L., et al. "Constituents of the Heartwood of Taiwan Yew" Tai'wan Ko'hsueh, vol. 38 (1984) pp. 119–125.

Yeh, M.K., et al. "Some Taxane Derivatives From the Heartwood of Taxus Mairei" J.Chin. Chem. Soc. 35, 309 (1988).

Zhang, Z., et al. "Taxanes From Taxus Yunnanensis"Phytochem. 29, 3673 (1990).

Bartholomew et al. "A Novel Rearrangement Reaction Conversion of 3–(Chloromethyl)azetidin–2–ones to Azetidine–3–carboxylic Acid Esters" Tetrahedron Letters, vol. 32, No. 36 (1981) pp. 4795–4798.

Chen et al. "Taxol Structure–Activity Relationships; Synthesis and Biological Evaluation of 2–Deoxytaxol" Tetrahedron Letters, vol. 34, No. 20, (1993) pp. 3205–3206.

Denis et al. "A Highly Efficient, Practical Approach to Natural Taxol" Journal of American Chemical Society, vol. 110 (1988) pp. 5917–5919.

Deutsch et al. "Synthesis of Congeners and Prodrugs. 3. Water–Soluble Prodrugs of Taxol With Potent Antitumor Actvity" Journal of Medicinal Chemistry, vol. 32, No. 4 (1989) pp. 788–792.

Farina et al. "The Chemistry of Taxanes: Unexpected Rearrangement of Baccatin III During Chemoselective Debenzoylation with Bu3SnOMe/LiCl" Tetrahedron Letters, vol. 33, No. 28 (1992) pp. 3979–3982.

Holton et al. "A Synthesis of Taxusin" Journal of the American Chemical Society, vol. 110 (1988) pp. 6558–6560.

Holton "Synthesis of the Taxane Ring System" Journal of the American Chemical Society, vol. 106 (1984) pp. 5731–5732.

Kaiser et al. "Synthesis of Esters of Acid–Unstable Alcohols by Means of n–Butyllithium" Journal of Organic Chemistry, vol. 35 (1970) pp. 1198–1199.

Klein "Synthesis of 9–Dihydrotaxol: A Novel Bioactive Taxane" Tetrahedron Letters, vol. 34, No. 13 (1993) pp. 2047–2050.

Magri et al. "Modified Taxols, 4. Synthesis and Biological Activity of Taxols Modified in the Side Chain" Journal of Natural Products, vol. 51, No. 2 (1988) pp. 298–306.

Miller et al. "Antileukemic Alkaloids form Taxus Wallichiana Zucc." Journal of Organic Chemistry, vol. 46 (1981) pp. 1469–1474.

Mukerjee et al. "B–Lactams: Retrospect and Prospect" Tetrahedron, vol. 34 (1978) pp. 1731–1767.

(List continued on next page.)

*Primary Examiner*—Ba K. Trinh
*Attorney, Agent, or Firm*—Senniger, Powers, Leavitt & Roedel

[57] ABSTRACT

A process for preparing N-acyl, N-sulfonyl and N-phosphoryl substituted isoserine esters in which a metal or an ammonium alkoxide is reacted with a β-lactam.

30 Claims, No Drawings

OTHER PUBLICATIONS

Ojima et al. "New and Efficient Approaches to the Semisynthesis of Taxol and its C–13 Side Chain Analogs By Means of B–Lactam Synthon Method" Tetrahedron, vol. 48, No. 34 (1992) pp. 6985–7012.

Samaranayake et al. "Modified Taxols. 5. Reaction of Taxol With Electrophilic Reagents and Preparation of a Rearranged Taxol Derivative with Tubulin Assembly Activity" Journal of Organic Chemistry, vol. 56 (1991) pp. 5114–5119.

Schultz et al. "Synthesis of New N–Radicals of Tetrazan--1-yl" Chemical Abstracts, vol. 108, No. 37298C (1988) p. 581.

Senilh et al. "Hemisynthese de nouveaux analogues du taxol. Etude de leur interaction avec la tubuline" C.R. Acad. S. Paris, Serie II, vol. 299, No. 15 Nov. 21 1984 pp. 1039–1043.

Wani et al. "Plant Antitumor Agents. VI. The Isolation and Structure of Taxol, A Novel Antileukemic and Antitumor Agent From Taxus brevifolia" Journal of the American Chemical Soc. vol. 93, No. 9 May 5 1971 pp. 2325–2327.

Witherup et al. "High Performance Liquid Chromatographic Separation of Taxol and Related Compounds From Taxus Brevifolia" Journal of Liquid Chromatography, vol. 12, No. 11 (1989) pp. 2117–2132.

METAL ALKOXIDES AND AMMONIUM ALKOXIDES

REFERENCE TO RELATED APPLICATIONS

"This application is a divisional application of U.S. Ser. No. 08/034,247, filed Mar. 22, 1993, now U.S. Pat. No. 5,430,160, which is a continuation-in-part application of U.S. Ser. No. 07/949,107, filed Sep. 22, 1992, now abandoned, which is a continuation-in-part of U.S. Serial No. 07/863,849, filed Apr. 6, 1992, now abandoned, which is a continuation-in-part application of U.S. Ser. No. 07/862,955, filed Apr. 3, 1992, now abandoned, which is a continuation-in-part application of U.S. Ser. No. 07/763,805, filed Sep. 23, 1991, now abandoned. This application is also a continuation-in-part application of U.S. Ser. No. 07/862,778, filed Apr. 3, 1992, now U.S. Pat. No. 5,229,526, which is a continuation-in-part application of U.S. Ser. No. 07/763,805, filed Sep. 23, 1991, now abandoned.

This invention was made with Government support under NIH Grant #CA 42031 and NIH Grant #CA 55131 awarded by the National Institutes of Health. The Government has certain rights in the invention.

BACKGROUND OF THE INVENTION

Three esters of N-acyl phenyl isoserine, taxol, taxotere and cephalomannine have been found to possess significant properties as antitumor agents. This application describes a process for the preparation of N-acyl, N-sulfonyl and N-phosphoryl substituted isoserine esters, in general and to a semi-synthesis for the preparation of taxane derivatives such as taxol, taxotere and other biologically active derivatives involving the use of metal alkoxides and β-lactams, in particular.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has the following structure:

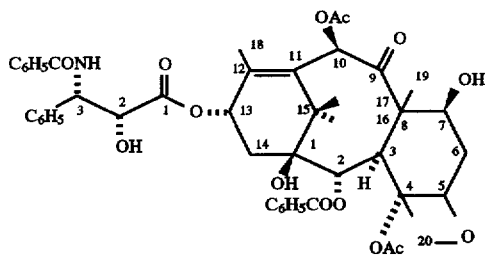

wherein Ac is acetyl. Because of this promising activity, taxol is currently undergoing clinical trials in both France and the United States.

The supply of taxol for these clinical trials is presently being provided by the bark from Taxus brevifollia (Western Yew). However, taxol is found only in minute quantities in the bark of these slow growing evergreens, causing considerable concern that the limited supply of taxol will not meet the demand. Consequently, chemists in recent years have expended their energies in trying to find a viable synthetic route for the preparation of taxol. So far, the results have not been entirely satisfactory.

One synthetic route that has been proposed is directed to the synthesis of the tetracyclic taxane nucleus from commodity chemicals. A synthesis of the taxol congener taxusin has been reported by Holton, et al. in JACS 110, 6558 (1988). Despite the progress made in this approach, the final total synthesis of taxol is, nevertheless, likely to be a multi-step, tedious, and costly process.

A semi-synthetic approach to the preparation of taxol has been described by Greene, et al. in JACS 110, 5917 (1988), and involves the use of a congener of taxol, 10-deacetyl baccatin III which has the structure of formula II shown below:

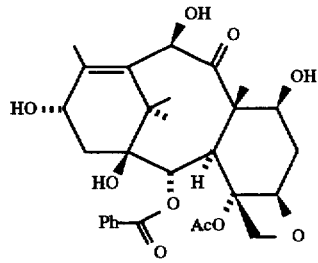

10-deacetyl baccatin III is more readily available than taxol since it can be obtained from the needles of Taxus baccata. According to the method of Greene et al., 10-deacetyl baccatin III is converted to taxol by attachment of the C-10 acetyl group and by attachment of the C-13 β-amido ester side chain through the esterification of the C-13 alcohol with a β-amido carboxylic acid unit. Although this approach requires relatively few steps, the synthesis of the β-amido carboxylic acid unit is a multi-step process which proceeds in low yield, and the coupling reaction is tedious and also proceeds in low yield. However, this coupling reaction is a key step which is required in every contemplated synthesis of taxol or biologically active derivative of taxol, since it has been shown by Wani, et al. in JACS 93, 2325 (1971) that the presence of the β-amido ester side chain at C13 is required for anti-tumor activity.

More recently, it has been reported in Colin et al. U.S. Pat. No. 4,814,470 that taxanes corresponding to the following formula III, have an activity significantly greater than that of taxol (I).

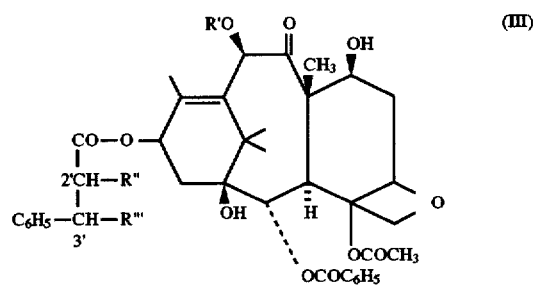

R' represents hydrogen or acetyl and one of R" and R'" represents hydroxy and the other represents tert-butoxycarbonylamino and their stereoisomeric forms, and mixtures thereof.

According to Colin et al., U.S. Pat. No. 4,418,470, the products of general formula (III) are obtained by the action of the sodium salt of tert-butyl N-chlorocarbamate on a product of general formula:

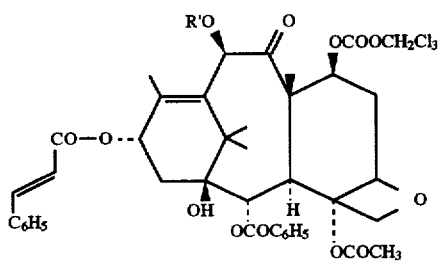

in which R' denotes an acetyl or 2,2,2-trichloroethoxycarbonyl radical, followed by the replacement of the 2,2,2-trichloroethoxycarbonyl group or groups by hydrogen. It is reported by Denis et al. in U.S. Pat. No. 4,924,011, however, that this process leads to a mixture of isomers which has to be separated and, as a result, not all the baccatin III or 10-deactylbaccatin III employed for the preparation of the product of general formula (IV) can be converted to a product of general formula (III). In an effort to improve upon the Colin et al. process, Denis et al. disclose a different process for preparing derivatives of baccatin III or of 10-deactylbaccatin III of general formula

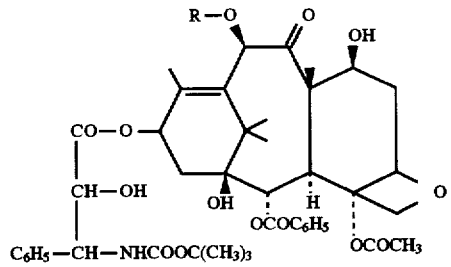

in which R' denotes hydrogen or acetyl wherein an acid of general formula:

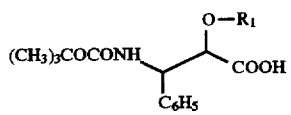

in which $R_1$ is a hydroxy-protecting group, is condensed with a taxane derivative of general formula:

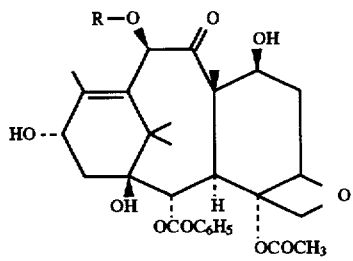

in which $R_2$ is an acetyl hydroxy-protecting group and $R_3$ is a hydroxy-protecting group, and the protecting groups $R_1$, $R_3$ and, where appropriate, $R_2$ are then replaced by hydrogen. However, this method employs relatively harsh conditions, proceeds with poor conversion, and provides less than optimal yields.

A major difficulty remaining in the synthesis of taxol and other potential anti-tumor agents is the lack of a readily available method for easy attachment, to the C-13 oxygen, of the chemical unit which provides the β-amido ester side chain. Development of such a process for its attachment in high yield would facilitate the synthesis of taxol as well as related anti-tumor agents having a modified set of nuclear substituents or a modified C-13 side chain. This need has been fulfilled by the discovery of a new, efficient process for attachment, to the C-13 oxygen, of the chemical unit which provides the β-amido ester side chain.

Another major difficulty encountered in the synthesis of taxol is that known processes for the attachment of the β-amido ester side chain at C-13 are generally not sufficiently diastereoselective. Therefore, the side chain precursor must be prepared in optically active form to obtain the desired diastereomer during attachment. The process of this invention, however, is highly diastereoselective, thus permitting the use of a racemic mixture of side chain precursor, eliminating the need for the expensive, time-consuming process of separating the precursor into its respective enantiomeric forms. The reaction additionally proceeds at a faster rate than previous processes, thus permitting the use of less side-chain precursor than has been required by such previous processes.

SUMMARY OF THE INVENTION

Among the objects of the present invention, therefore, is the provision of a process for the preparation of N-acyl, N-sulfonyl and N-phosphoryl esters of isoserine; the provision of a side chain precursor for the synthesis of taxane derivatives; the provision of a process for the attachment of the side chain precursor in relatively high yield to provide an intermediate which is readily converted to the desired taxane derivative; and the provision of such a process which is highly diastereoselective.

In accordance with the present invention, a process is provided for the preparation of isoserine esters having the formula

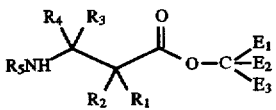

comprising reacting a β-lactam with an alkoxide, the β-lactam having the formula

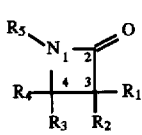

and the alkoxide having the formula

$MOCE_1E_2E_3$ wherein $R_1$ is —$OR_6$, —$SR_7$, or —$NR_8R_9$;

$R_2$ is hydrogen, alkyl, alkenyl, alkynyl, aryl, or heteroaryl;

$R_3$ and $R_4$ are independently hydrogen, alkyl, alkenyl, alkynyl, aryl, heteroaryl, acyl or heterosubstituted alkyl, alkenyl, alkynyl, aryl or heteroaryl, provided, however, that $R_3$ and $R_4$ are not both acyl;

$R_5$ is —$COR_{10}$, —$COOR_{10}$, —$COSR_{10}$, —$CONR_8R_{10}$, or —$SO_2R_{11}$, $R_6$ is hydrogen, alkyl, alkenyl, alkynyl, aryl, heteroaryl, hydroxy protecting group, or a functional group which increases the water solubility of the taxane derivative, $R_7$ is alkyl, alkenyl, alkynyl, aryl, heteroaryl, or sulfhydryl protecting group, $R_8$ is hydrogen, alkyl, alkenyl, alkynyl, aryl, heteroaryl, or heterosubstituted alkyl, alkenyl, alkynyl, aryl or heteroaryl;

$R_9$ is an amino protecting group;

$R_{10}$ is alkyl, alkenyl, alkynyl, aryl, heteroaryl, or heterosubstituted alkyl, alkenyl alkynyl, aryl or heteroaryl;

$R_{11}$ is alkyl, alkenyl, alkynyl, aryl, heteroaryl, —$OR_{10}$, or —$NR_8R_{14}$;

$R_{14}$ is hydrogen, alkyl, alkenyl, alkynyl, aryl, or heteroaryl;

$E_1$, $E_2$ and $E_3$ are independently hydrogen, hydrocarbon or cyclic, provided, at least one of $E_1$, $E_2$ and $E_3$ is other than hydrogen; and M comprises ammonium or is a metal.

In accordance with another aspect of the present invention, the alkoxide and β-lactam are selected so as to provide a process for preparing taxol, taxotere and other biologically active taxane derivatives having the following structural formula:

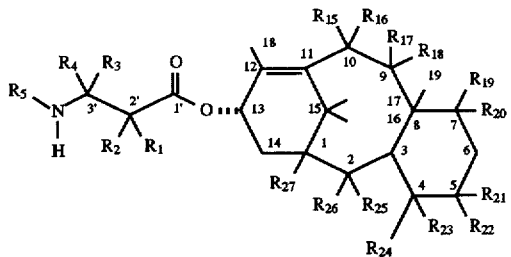

wherein $R_1$–$R_{14}$ are as previously defined, $R_{15}$ is hydrogen or together with $R_{16}$ forms an oxo, $R_{16}$ is hydrogen, —$OCOR_{29}$, hydroxy, or protected hydroxy, or together with $R_{15}$ forms an oxo;

$R_{17}$ is hydrogen or together with $R_{18}$ forms an oxo, $R_{18}$ is hydrogen, hydroxy, protected hydroxy, acyloxy, or together with $R_{17}$ forms an oxo;

$R_{19}$ is hydrogen or together with $R_{20}$ forms an oxo, $R_{20}$ is hydrogen, halogen, protected hydroxy, —$OR_{28}$, or together with $R_{19}$ forms an oxo;

$R_{21}$ is hydrogen or together with $R_{22}$ forms an oxo, $R_{22}$ is hydrogen, hydroxy, protected hydroxy, acyloxy, together with $R_{21}$ forms an oxo, or together with $R_{23}$ and the carbon atoms to which they are attached form an oxetane ring;

$R_{23}$ is hydrogen, together with $R_{24}$ forms an oxo, or together with $R_{22}$ and the carbon atoms to which they are attached form an oxetane ring;

$R_{24}$ is hydrogen, alkyl, alkenyl, alkynyl, aryl, heteroaryl, cyano, hydroxy, —$OCOR_{30}$, or together with $R_{23}$ forms an oxo, oxirane or methylene;

$R_{25}$ is hydrogen, hydroxy, or —$OCOR_{31}$;

$R_{26}$ is hydrogen or taken together with $R_{25}$ forms an oxo;

$R_{27}$ is hydrogen, hydroxy, protected hydroxy;

$R_{28}$ is hydrogen, acyl, hydroxy protecting group or a functional group which increases the solubility of the taxane derivative; and $R_{29}$, $R_{38}$, and $R_{31}$ are independently hydrogen, alkyl, alkenyl, alkynyl, monocyclic aryl or monocyclic heteroaryl Briefly, therefore, the taxane derivatives are prepared by reacting a β-lactam (2) with an alkoxide having the bi-, tri- or tetracyclic taxane nucleus to form a β-amido ester intermediate. The intermediate is then converted to the taxane derivative. β-lactam (2) has the general formula:

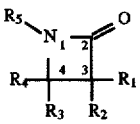

wherein $R_1$–$R_5$ are as previously defined. The alkoxide preferably has the tricyclic taxane nucleus corresponding to the general formula:

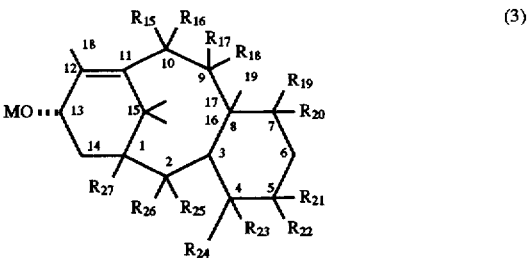

wherein M and $R_{15}$–$R_{27}$ are as previously defined. Most preferably, the alkoxide has the tetracyclic taxane nucleus corresponding to alkoxide (3) wherein $R_{22}$ and $R_{23}$ together form an oxetane ring.

Other objects and features of this invention will be in part apparent and in part pointed out hereinafter.

DETAILED DESCRIPTION

As used herein "Ar" means aryl; "Ph" means phenyl; "Ac" means acetyl; "Et" means ethyl; "R" means alkyl unless otherwise defined; "Bu" means butyl; "Pr" means propyl; "TES" means triethylsilyl; "TMS" means trimethylsilyl; "TPAP" means tetrapropylammonium perruthenate; "DMAP" means p-dimethylamino pyridine; "DMF" means dimethylformamide; "LDA" means lithium diisopropylamide; "LAH" means lithium aluminum hydride; "Red-Al" means sodium bis(2-methoxyethoxy) aluminum hydride; "AIBN" means azo-(bis)-isobutyronitrile "10-DAB" means 10-desacetylbaccatin III; protected hydroxy means -13 OR wherein R is a hydroxy protecting group; sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothio-pyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2, 2-trichloroethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, hexyl and the like.

The alkenyl groups described herein, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, hexenyl, and the like.

The alkynyl groups described herein, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, hexynyl, and the like.

The aryl moieties described herein, either alone or with various substituents, contain from 6 to 15 carbon atoms and include phenyl. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described herein, either alone or with various substituents, contain from 5 to 15 atoms and include, furyl, thienyl, pyridyl and the like. Substituents include alkanoxy, protected hydroxy, halogen, alkyl, aryl, alkenyl, acyl, acyloxy, nitro, amino, and amido.

The acyloxy groups described herein contain alkyl, alkenyl, alkynyl, aryl or heteroaryl groups.

The heterosubstituents of the heterosubstituted alkyl, alkenyl, alkynyl, aryl, and heteroaryl moieties described herein, contain nitrogen, oxygen, sulfur, halogens and/or one to six carbons, and include lower alkoxy such as methoxy, ethoxy, butoxy, halogen such as chloro or fluoro, and nitro.

The present invention is directed to a process for preparing substituted isoserine esters, in general, and taxol, taxotere and other taxane derivatives which are biologically active using β-lactam (2), the structure of which is depicted hereinbelow:

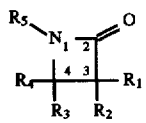

wherein $R_1$, $R_2$, $R_3$, $R_4$ and $R_5$ are as previously defined.

In accordance with the present invention, $R_5$ of β-lactam (2) is preferably —$COR_{10}$ or —$COOR10$ with $R_{10}$ being lower alkyl, aryl, heteroaryl (such as furyl or thienyl), or substituted phenyl, and most preferably phenyl, methyl, ethyl, tert-butyl, or

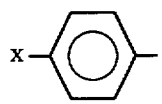

wherein X is Cl, Br, F, $CH_3O$—, or $NO_2$—. Preferably $R_2$ and $R_4$ are hydrogen or lower alkyl. $R_3$ is preferably aryl, most preferably, naphthyl, phenyl,

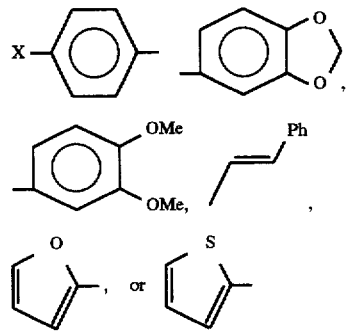

wherein X is as previously defined, Me is methyl and Ph is phenyl. Preferably, $R_1$ is selected from —$OR_6$, —$SR_7$ or —$NR_8R_9$ wherein $R_6$, $R_7$ and $R_9$, are hydroxy, sulfhydryl, and amine protecting groups, respectively, and $R_8$ is hydrogen, alkyl, alkenyl, alkynyl, aryl, or heteroaryl. Most preferably, $R_1$ is —$OR_6$ wherein $R_6$ is triethylsilyl ("TES"), 1-ethoxyethyl ("EE") or 2,2,2-trichloroethoxymethyl.

As noted above, $R_1$ of β-lactam (2) may be —$OR_6$ with $R_6$ being alkyl, acyl, ethoxyethyl ("EE"), triethylsilyl ("TES"), 2,2,2-trichloroethoxymethyl, or other hydroxyl protecting group such as acetals and ethers, i.e., methoxymethyl ("MOM"), benzyloxymethyl; esters, such as acetates; carbonates, such as methyl carbonates; and alkyl and aryl silyl such as triethylsilyl, trimethylsilyl, dimethyl-t-butylsilyl, dimethylarylsilyl, dimethylheteroarylsilyl, and triisopropylsilyl, and the like. A variety of protecting groups for the hydroxyl group and the synthesis thereof may be found in "Protective Groups in Organic Synthesis" by T. W. Greene, John Wiley and Sons, 1981. The hydroxyl protecting group selected should be easily removed under conditions that are sufficiently mild, e.g., in 48% HF, acetonitrile, pyridine, or 0.5% HCl/water/ethanol, and/or zinc, acetic acid so as not to disturb the ester linkage or other substituents of the taxol intermediate. However, $R_6$ is preferably triethylsilyl, 1-ethoxyethyl or 2,2,2-trichloroethoxymethyl, and most preferably triethylsilyl.

Since β-lactam (2) has several asymmetric carbons, it is known to those skilled in the art that the compounds of the present invention having asymmetric carbon atoms may exist in diastereomeric, racemic, or optically active forms. All of these forms are contemplated within the scope of this invention. More specifically, the present invention includes enantiomers, diastereomers, racemic mixtures, and other mixtures thereof.

β-lactam (2) can be prepared from readily available materials, as is illustrated in schemes A and B below:

Scheme A

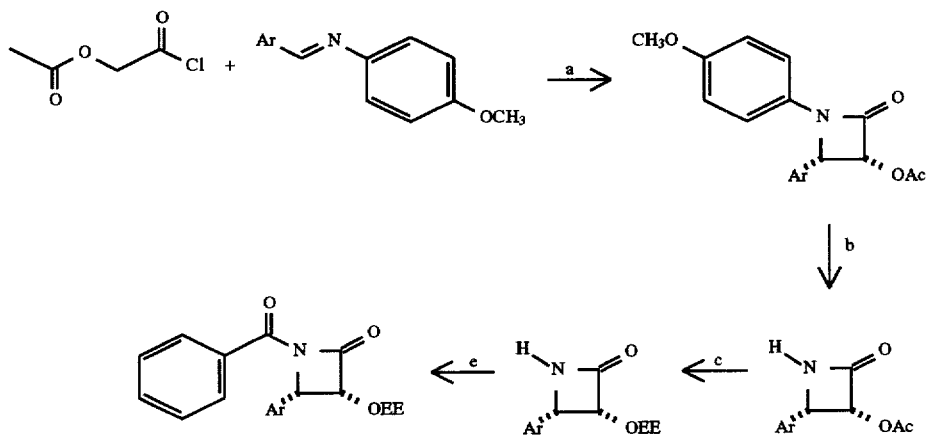

Scheme B

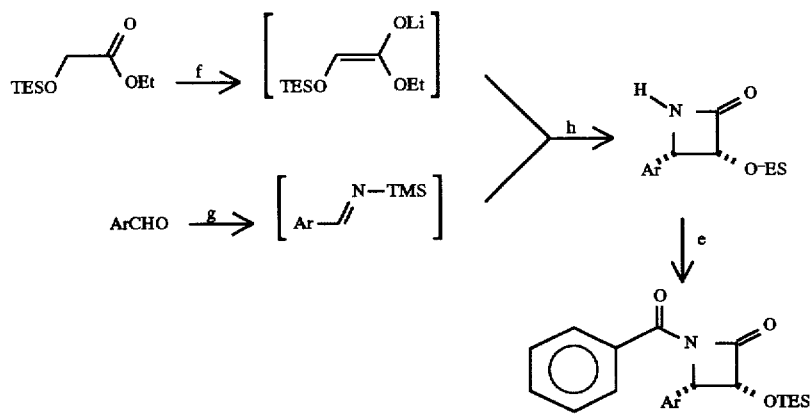

reagents: (a) triethylamine, CH$_2$Cl$_2$, 25° C., 18 h; (b) 4 equiv ceric ammonium nitrate, CH$_3$CN, −10° C., 10 min; (c) KOH, THF, H$_2$O, 0° C., 30 min; (d) ethyl vinyl ether, THF, toluene sulfonic acid (cat.), 0° C., 1.5 h; (e) n-butyllithium, ether, −78° C., 10 min; benzoyl chloride, −78° C., 1 h; (f) lithium diisopropyl amide, THF −78° C. to −50° C.; (g) lithium hexamethyldisilazide, THF −78° C. to 0° C.; (h) THF, −78° C. to 25° C., 12 h.

The starting materials are readily available. In scheme A, α-acetoxy acetyl chloride is prepared from glycolic acid, and, in the presence of a tertiary amine, it cyclocondenses with imines prepared from aldehydes and p-methoxyaniline to give 1-p-methoxyphenyl-3-acyloxy-4-arylazetidin-2-ones. The p-methoxyphenyl group can be readily removed through oxidation with ceric ammonium nitrate, and the acyloxy group can be hydrolyzed under standard conditions familiar to those experienced in the art to provide 3-hydroxy-4-arylazetidin-2-ones. The 3-hydroxyl group is protected with 1-ethoxyethyl, but may be protected with variety of standard protecting groups such as the triethylsilyl group or other trialkyl (or aryl) silyl groups. In Scheme B, ethyl-α-triethylsilyloxyacetate is readily prepared from glycolic acid.

The racemic β-lactams may be resolved into the pure enantiomers prior to protection by recrystallization of the corresponding 2-methoxy-2-(trifluoromethyl) phenylacetic esters. However, the reaction described hereinbelow in which the β-amido ester side chain is attached has the advantage of being highly diastereoselective, thus permitting the use of a racemic mixture of side chain precursor.

The 3-(1-ethoxyethoxy)-4-phenylazetidin-2-one of scheme A and the 3-(1-triethylsilyloxy)-4-phenylazetidin-2-one of scheme B can be converted to β-lactam (2), by treatment with a base, preferably n-butyllithium, and an acyl chloride, alkylchloroformate, sulfonyl chloride, phosphinyl chloride or phosphoryl chloride at −78° C. or below.

The process of the present invention is particularly useful for the esterification of mono- or polycyclic alkoxides represented by the formula

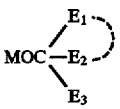

in which E$_1$, E$_2$ and the carbon to which they are attached define a carbocyclic and/or heterocyclic skeleton which may be mono- or polycyclic and E$_3$ is hydrogen or hydrocarbon, preferably lower alkyl. Most preferably, the carbocyclic and/or heterocyclic skeleton comprises about 6 to 20 atoms and the hetero atoms are oxygen. The cyclic skeleton may be hydrocarbon and/or heterosubstituted with heterosubstituents including, for example, esters, ethers, amines, alcohols, protected alcohols, carbonyl groups, halogens, oxygen, substituted oxygen or substituted nitrogen.

When the alkoxides have the bi-, tri- or tetracyclic taxane nucleus, the process of the present invention may advantageously be used to prepare taxane derivatives, many of which have been found to have significant biological activity. As used herein, an alkoxide having the bicyclic taxane nucleus has the carbocyclic skeleton corresponding to rings A and B of metal alkoxide (3):

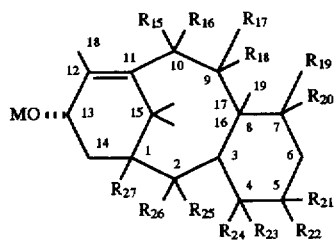

wherein M and $R_{15}$–$R_{27}$ are as previously defined. An alkoxide having the tricyclic taxane nucleus has the carbocyclic skeleton corresponding to rings A, B and C of metal alkoxide (3). An alkoxide having the tetracyclic taxane nucleus has carbocyclic rings A, B and C of metal alkoxide (3) and the oxetane ring defined by $R_{22}$, $R_{23}$, and the carbons to which they are attached.

Substituent, M, of alkoxide 3 is a metal or comprises ammonium. The metal may be a Group IA, IIA, transition (including lanthanides and actinides), IIB, IIIA IVA, VA, or VIA metal (CAS version). The ammonium comprising substituent is preferably tetraalkylammonium and the alkyl component of the tetraalkylammonium substituent is preferably $C_1$–$C_{10}$ alkyl such as methyl or butyl.

Alkoxides (3) are prepared by reacting an alcohol having two to four rings of the taxane nucleus and a C-13 hydroxyl group with an organometallic compound, zinc chloride dimethoxyethane complex, anhydrous cadmium chloride, or a tetraalkylammonium halide such as tetrabutylammonium chloride in a suitable solvent. Preferably, the alcohol is a derivative of baccatin III or 10-deacetyl baccatin III having the structure:

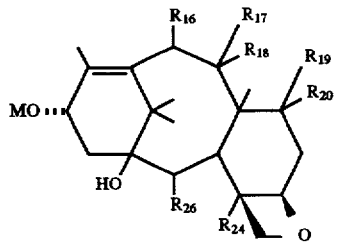

wherein $R_{16}$–$R_{20}$, $R_{24}$, and $R_{26}$ are as previously defined. More preferably, $R_{16}$ is protected hydroxy or —$OCOR_{29}$, $R_{19}$ is hydrogen, $R_{20}$ is hydrogen, halogen or protected hydroxy, $R_{24}$ is acetoxy, and $R_{26}$ is benzoyloxy. Most preferably, the alcohol is a protected baccatin III, in particular, 7-O-triethylsilyl baccatin III (which can be obtained as described by Greene, et al. in JACS 110, 5917 (1988) or by other routes) or 7,10-bis-O-triethylsilyl baccatin III.

As reported in Greene et al., 10-deacetyl baccatin III is converted to 7-O-triethylsilyl-10-deacetyl baccatin III according to the following reaction scheme:

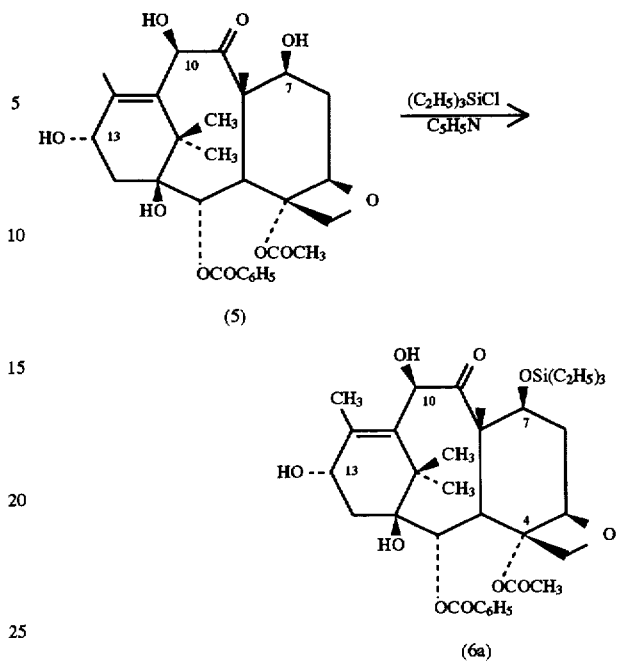

Under what is reported to be carefully optimized conditions, 10-deacetyl baccatin III is reacted with 20 equivalents of $(C_2H_5)_3SiCl$ at 23° C. under an argon atmosphere for 20 hours in the presence of 50 ml of pyridine/mmol of 10-deacetyl baccatin III to provide 7-triethylsilyl-10-deacetyl baccatin III (6a) as a reaction product in 84–86% yield after purification. The reaction product is then acetylated with 5 equivalents of $CH_3COCl$ and 25 mL of pyridine/mmol of (6a) at 0° C. under an argon atmosphere for 48 hours to provide 86% yield of 7-O-triethylsilyl baccatin III (6b). Greene, et al. in JACS 110, 5917 at 5918 (1988).

Alternatively, 7-triethylsilyl-10-deacetyl baccatin III (6a) can be protected at C-10 oxygen with an acid labile hydroxyl protecting group. For example, treatment of with n-butyllithium in THF followed by triethylsilyl chloride (1.1 mol equiv.) at 0° C. gives 7,10-bis-O-triethylsilyl baccatin III (6c) in 95% yield. Also, (6a) can be converted to 7-O-triethylsilyl-10-(1-ethoxyethyl) baccatin III (6d) in 90% yield by treatment with excess ethyl vinyl ether and a catalytic amount of methane sulfonic acid. These preparations are illustrated in the reaction scheme below.

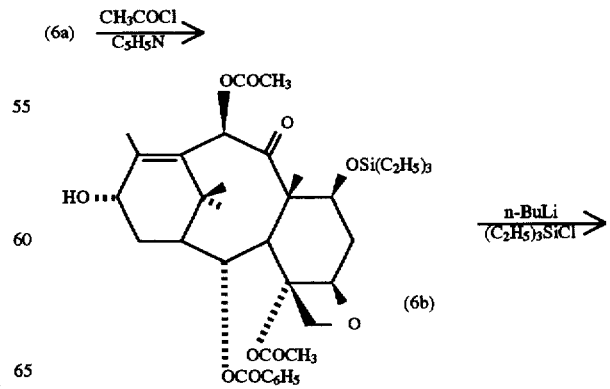

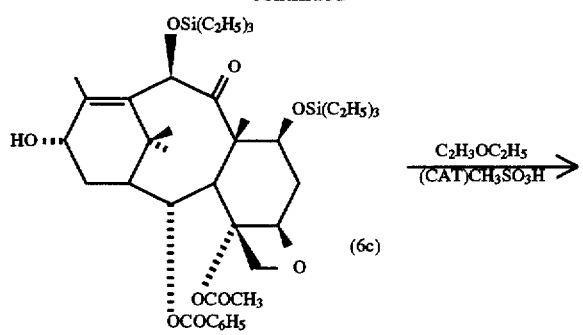

(6c)

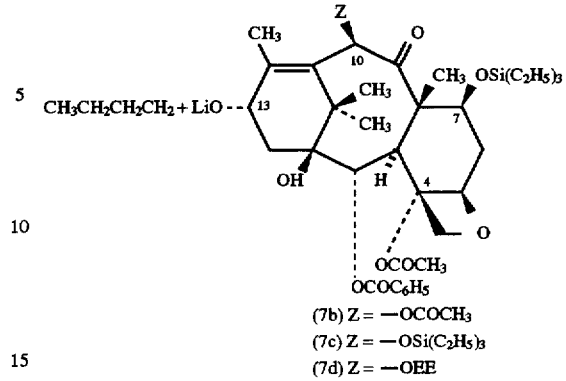

(7b) Z = —OCOCH₃
(7c) Z = —OSi(C₂H₅)₃
(7d) Z = —OEE

7-O-triethylsilyl baccatin III (6b), 7,10-bis-O-triethylsilyl baccatin III (6c), or 7-O-triethylsilyl-10-(1-ethoxyethyl) baccatin III (6d) is reacted with an organometallic compound such as n-butyllithium in a solvent such as tetrahydrofuran (THF), to form the metal alkoxide 13-O-lithium-7-O-triethylsilyl baccatin III (7b) 13-O-lithium-7,10-bis-O-triethylsilyl baccatin III (7c), or 13-O-lithium-7-O-triethylsilyl-10-(1-ethoxyethyl) baccatin III (7d) as shown in the following reaction scheme:

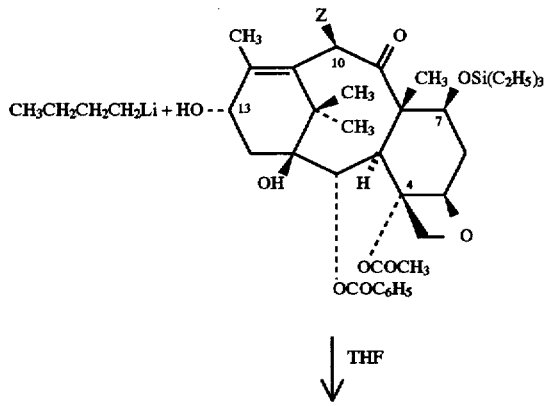

As illustrated in the following reaction scheme, a suitable metal alkoxide of the present invention such as 13-O-lithium-7-O-triethylsilyl baccatin III derivative (7b, 7c, or 7d) reacts with a β-lactam of the present invention to provide an intermediate (8b, 8c, or 8d) in which the C-7 hydroxyl group is protected with a triethylsilyl or 1-ethoxyethyl group.

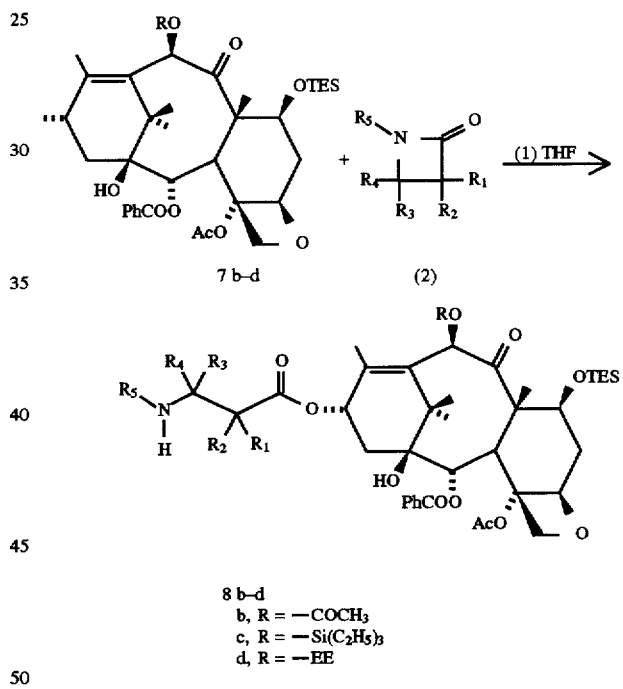

8 b–d
b, R = —COCH₃
c, R = —Si(C₂H₅)₃
d, R = —EE

Intermediate compound (8b) readily converts to taxol when $R_1$ is —OR₆, $R_2$ and $R_3$ are hydrogen, $R_4$ is phenyl, $R_5$ is benzoyl and $R_6$ is a hydroxy protecting group such as triethylsilyl. Intermediate compound (8c) readily converts to taxotere when $R_1$ is —OR₆, $R_2$ and $R_3$ are hydrogen, $R_4$ is phenyl, $R_5$ is tertbutoxycarbonyl and $R_6$ is a hydroxy protecting group such as triethylsilyl. Intermediate compound (8d) readily converts to 10-deacetyl taxol when $R_1$ is $-OR_6$, $R_2$ and $R_3$ are hydrogen, $R_4$ is phenyl, $R_5$ is benzoyl, and $R_6$ is a hydroxy protecting group such as triethylsilyl. Intermediate compounds (8b, 8c and 8d) may be converted to the indicated compounds by hydrolyzing the triethylsilyl and 1-ethoxyethyl groups under mild conditions so as not to disturb the ester linkage or the taxane derivative substituents.

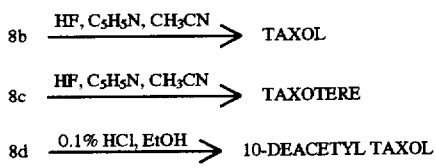

Both the conversion of the alcohol to the metal alkoxide and the ultimate synthesis of the taxol can take place in the same reaction vessel. Preferably, the β-lactam is added to the reaction vessel after formation therein of the metal alkoxide.

The organometallic compound n-butyllithium is preferably used to convert the alcohol to the corresponding metal alkoxide, but other sources of metallic substituent such as lithium diisopropyl amide, other lithium or magnesium amides, ethylmagnesium bromide, methylmagnesium bromide, other organolithium compounds, other organomagnesium compounds, organosodium, organotitanium, organozirconium, organozinc, organocadmium or organopotassium or the corresponding amides may also be used. Organometallic compounds are readily available, or may be prepared by available methods including reduction of organic halides with metal. Lower alkyl halides are preferred. For example, butyl bromide can be reacted with lithium metal in diethyl ether to give a solution of n-butyllithium in the following manner:

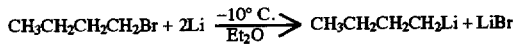

Alternatively, the lithium alkoxide may be induced to undergo exchange with metal halides to form alkoxides of aluminum, boron, cerium, calcium, zirconium or zinc.

Although THF is the preferred solvent for the reaction mixture, other ethereal solvents, such as dimethoxyethane, or aromatic solvents may also be suitable. Certain solvents, including some halogenated solvents and some straight-chain hydrocarbons in which the reactants are too poorly soluble, are not suitable. Other solvents are not appropriate for other reasons. For example, esters are not appropriate for use with certain organometallic compounds such as n-butyllithium due to incompatibility therewith.

Although the reaction scheme disclosed herein is directed to the synthesis of certain taxol derivatives, it can be used with modifications in either the β-lactam or the tetracyclic metal alkoxide. Therefore, alkoxides other than 13-O-lithium-7-O-triethylsilyl baccatin III may be used to form a taxol or other taxanes according to the method of this invention. The β-lactam and the tetracyclic alkoxide can be derived from natural or unnatural sources, to prepare other synthetic taxols, taxol derivatives, 10-deacetyltaxols, and the enantiomers and diastereomers thereof contemplated within the present invention.

The process of the invention also has the important advantage of being highly diastereoselective. Therefore racemic mixtures of the side chain precursors may be used. Substantial cost savings may be realized because there is no need to resolve racemic β-lactams into their pure enantiomers. Additional cost savings may be realized because less side chain precursor, e.g., 60–70% less, is required relative to prior processes.

The water solubility of compounds of formula (3) may be improved by modification of the C2' and/or C7 substituents. For instance, water solubility may be increased if $R_1$ is $-OR_6$ and $R_{20}$ is $-OR_{28}$, and $R_6$ and $R_{28}$ are independently hydrogen or $-COGCOR^1$ wherein G is ethylene, propylene, $-CH=CH-$, 1,2-cyclohexane, or 1,2-phenylene.

$R^1 = OH$ base, $NR^2R^3$, $OR^3$, $SR^3$, $OCH_2CONR^4R^5$, OH $R^2 =$ hydrogen, methyl $R^3 = (CH_2)_n NR_6R_7$; $(CH_2)_n N^{\oplus} R^6 R^7 R^8 X^{\ominus}$ n = 1 to 3

$R^4 =$ hydrogen, lower alkyl containing 1 to 4 carbons $R^5 =$ hydrogen, lower alkyl containing 1 to 4 carbons, benzyl, hydroxyethyl, $CH_2CO_2H$, dimethylaminoethyl $R^6R^7 =$ lower alkyl containing 1 or 2 carbons, benzyl or $R^6$ and $R^7$ together with the nitrogen atom of $NR^6R^7$ form the following rings

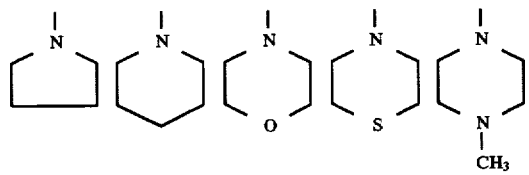

$R^8 =$ lower alkyl containing 1 or 2 carbons, benzyl $X^\ominus =$ halide base $= NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH. The preparation of compounds in which $X_1$ or $X_2$ is $-COGCOR^1$ is set forth in Hangwitz U.S. Pat. 4,942,184 which is incorporated herein by reference.

Alternatively, water solubility may be increased when $R_1$ is $-OR_6$ and $R_6$ is a radical having the formula $-COCX=CHX$ or $-COX-CHX-CHX-SO_2O-M$ wherein X is hydrogen, alkyl or aryl and M is hydrogen, alkaline metal or an ammonio group as described in Kingston et al., U.S. Pat. No. 5,059,699 (incorporated herein by reference).

Taxanes having alternative C9 keto substituent may be prepared by selectively reduction to yield the corresponding C9 β-hydroxy derivative. The reducing agent is preferably a borohydride and, most preferably, tetrabutylammoniumborohydride ($Bu_4NBH_4$) or triacetoxyborohydride.

As illustrated in Reaction Scheme 1, the reaction of baccatin III with $Bu_4NBH_4$ in methylene chloride yields 9-desoxo-9β-hydroxybaccatin III 5. After the C7 hydroxy group is protected with the triethylsilyl protecting group, for example, a suitable side chain may be attached to 7-protected-9β-hydroxy derivative 6 as elsewhere described herein. Removal of the remaining protecting groups thus yields 9β-hydroxy-desoxo taxol or other 9β-hydroxytetracylic taxane having a C13 side chain.

REACTION SCHEME 1

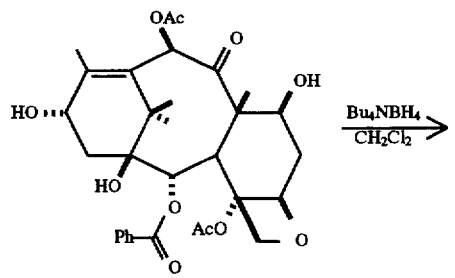

5

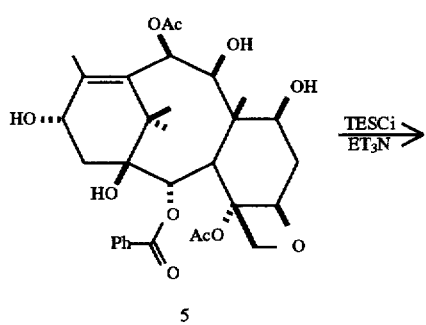

5

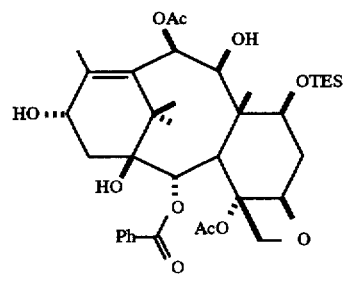

6

-continued
REACTION SCHEME 1

Alternatively, the C13 hydroxy group of 7-protected-9β-hydroxy derivative 6 may be protected with trimethylsilyl or other protecting group which can be selectively removed relative to the C7 hydroxy protecting group as illustrated in Reaction Scheme 2, to enable further selective manipulation of the 1 various substituents of the taxane. For example, reaction of 7,13-protected-9β-hydroxy derivative 7 with KH causes the acetate group to migrate from C10 to C9 and the hydroxy group to migrate from C9 to C10, thereby yielding 10-desacetyl derivative 8. Protection of the C10 hydroxy group of 10-desacetyl derivative 8 with triethylsilyl yields derivative 9. Selective removal of the C13 hydroxy protecting group from derivative 9 yields derivative 10 to which a suitable side chain may be attached as described above.

REACTION SCHEME 2

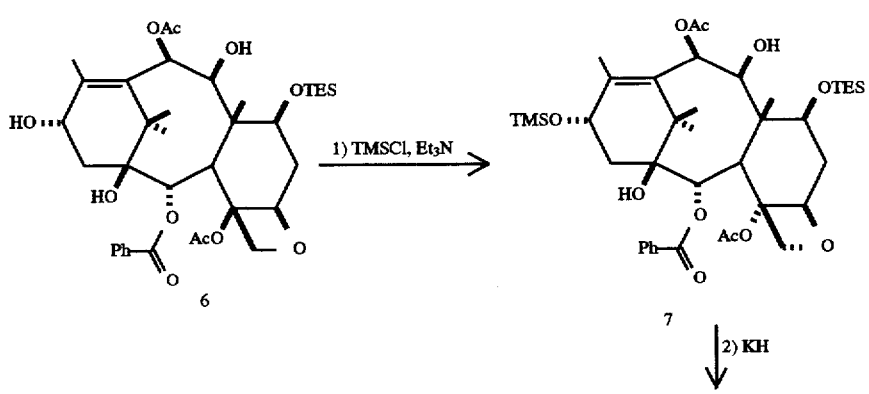

-continued
REACTION SCHEME 2

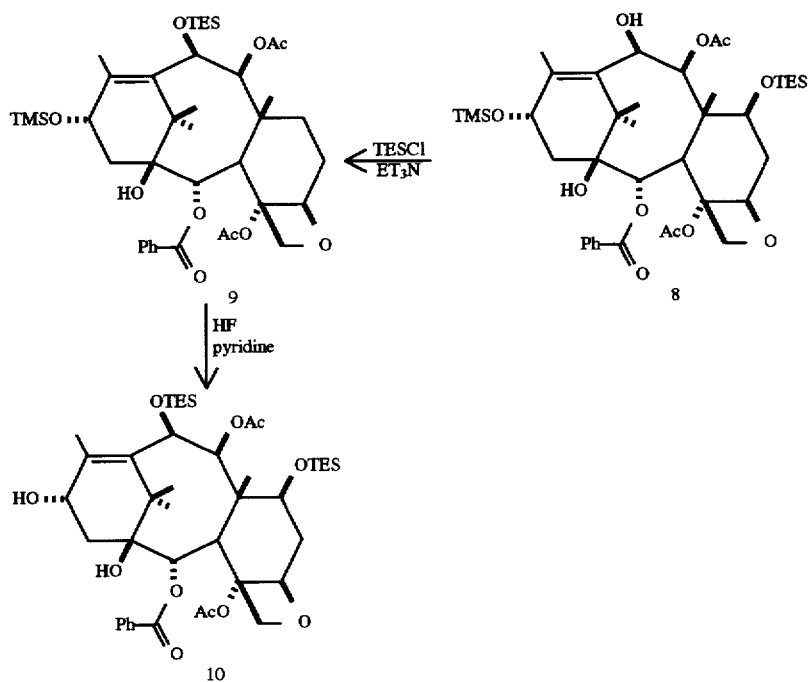

As shown in Reaction Scheme 3, 10-oxo derivative 11 can be provided by oxidation of 10-desacetyl derivative 8. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 11 with a reducing agent such as samarium diiodide to yield 9-desoxo-10-oxo derivative 12 from which the C13 hydroxy protecting group can be selectively removed followed by attachment of a side chain as described above to yield 9-desoxo-10-oxo-taxol or other 9-desoxo-10-oxotetracylic taxanes having a C13 side chain.

REACTION SCHEME 3

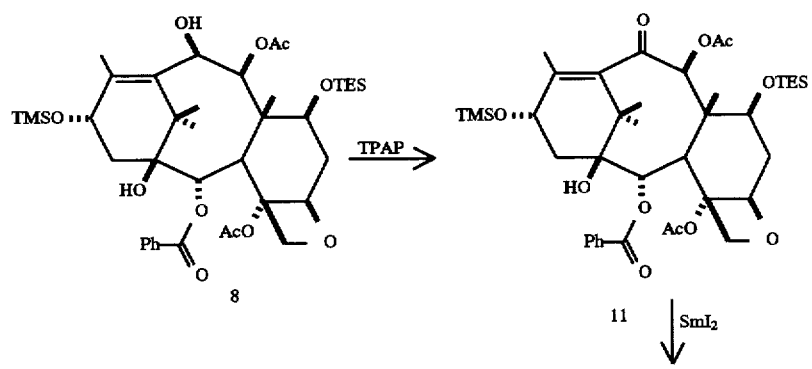

-continued
REACTION SCHEME 3

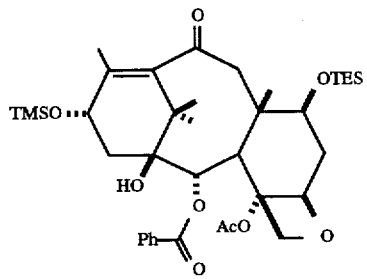

12

Reaction Scheme 4 illustrates a series of reactions in which 10-DAB is used as the starting material. Reduction of 10-DAB yields pentaol 13, the C7 and C10 hydroxyl groups of which can be selectively protected with the triethylsilyl or another protecting group to produce triol 14. A C13 side chain can be attached to triol 14 as described above or, alternatively, after further modification of the tetracyclic substituents.

material as illustrated in Reaction Scheme 5. Reaction of -DAB with triethylsilyl chloride in pyridine yields 7-protected 10-DAB 15. The C10 hydroxy substituent of 7-protected 10-DAB 15 may then be readily acylated with any standard acylating agent to yield derivative 16 having a new C10 acyloxy substituent. Selective reduction of the C9 keto substituent of derivative 16 yields 9β-hydroxy derivative 17 to which a C13 side chain may be attached.

REACTION SCHEME 4

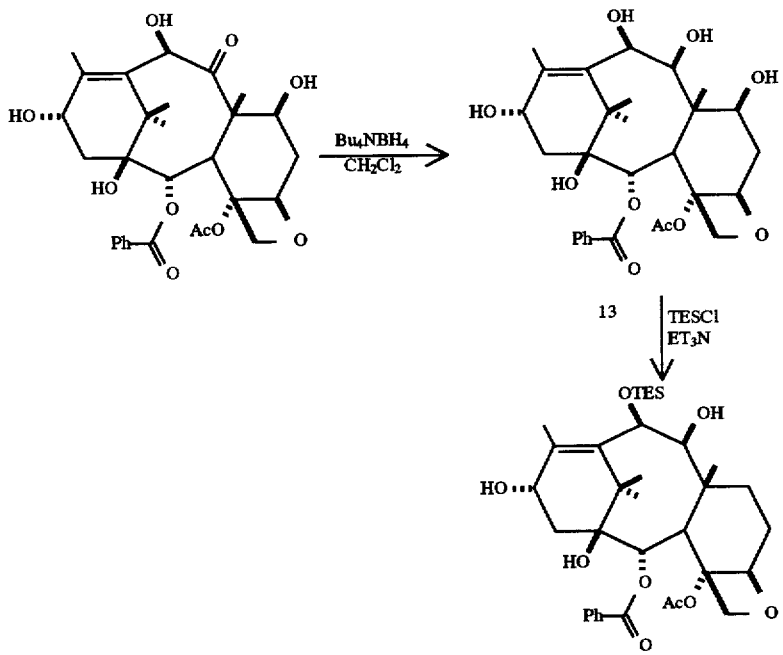

Taxanes having C9 and/or C10 acyloxy substituents other than acetate can be prepared using 10-DAB as a starting Alternatively, the C10 and C9 groups can be caused to migrate as set forth in Reaction Scheme 2, above.

REACTION SCHEME 5

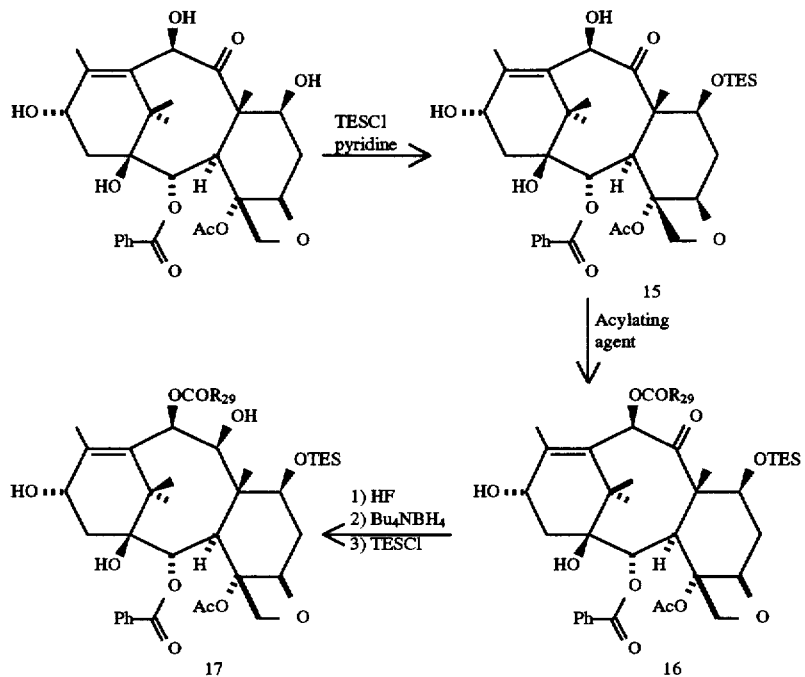

Taxanes having alternative C2 and/or C4 esters can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride.

Baccatin III and 10-DAB analogs having different substituents at C2 and/or C4 can be prepared as set forth in Reaction Schemes 6–10. To simplify the description, 10-DAB is used as the starting material. It should be understood, however, that baccatin III derivatives or analogs may be produced using the same series of reactions (except for the protection of the C10 hydroxy group) by simply replacing 10-DAB with baccatin III as the starting material. 9-desoxo derivatives of the baccatin III and 10-DAB analogs having different substituents at C2 and/or C4 can then be prepared by reducing the C9 keto substituent of these analogs and carrying out the other reactions described above.

In Reaction Scheme 6, protected 10-DAB 3 is converted to the triol 18 with lithium aluminum hydride. Triol 18 is then converted to the corresponding $C^2$ ester using $Cl_2CO$ in pyridine followed by a nucleophilic agent (e.g., Grignard reagents or alkyllithium reagents).

Scheme 6

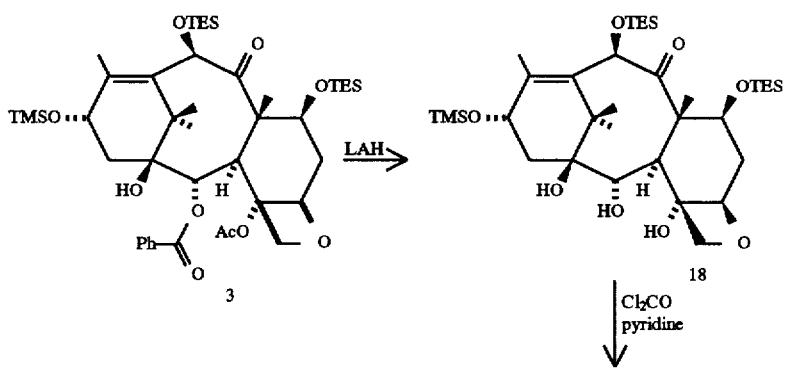

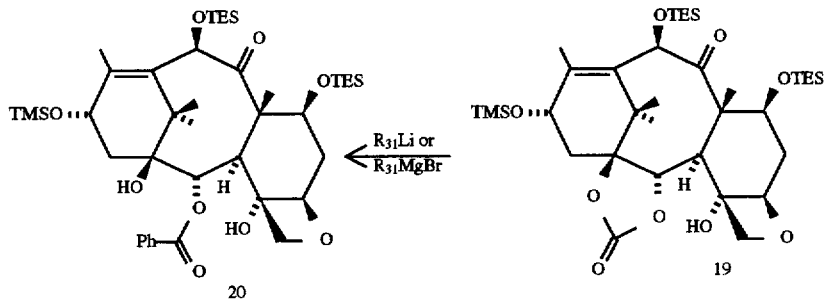

Alternatively, deprotonation of triol 18 with LDA followed by introduction of an acid chloride selectively gives the C4 ester. For example, when acetyl chloride was used, triol 18 was converted to 1,2 diol 4 as set forth in Reaction Scheme 7.

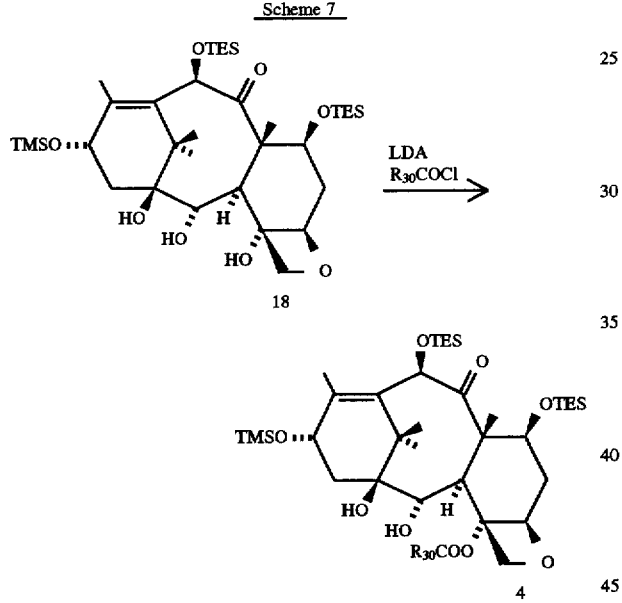

As set forth in Reaction Scheme 9, other C4 substituents can be provided by reacting carbonate 19 with an acid chloride and a tertiary amine to yield carbonate 22 which is then reacted with alkyllithiums or Grignard reagents to provide 10-DAB derivatives having new substituents at C2.

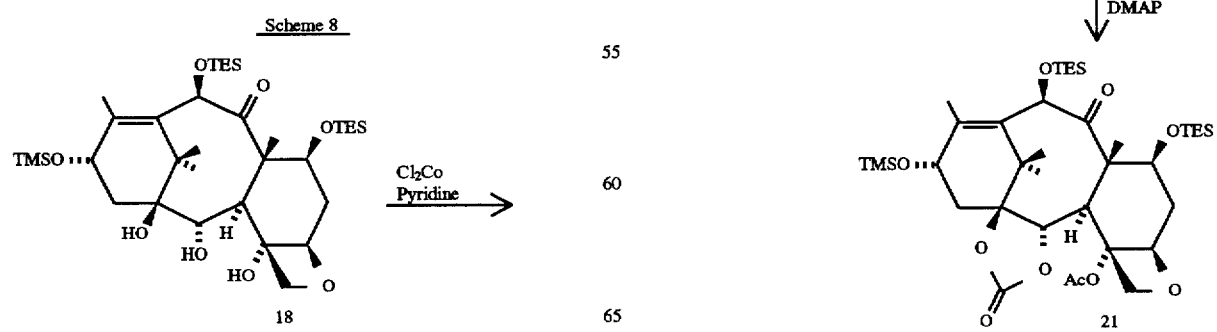

Scheme 9

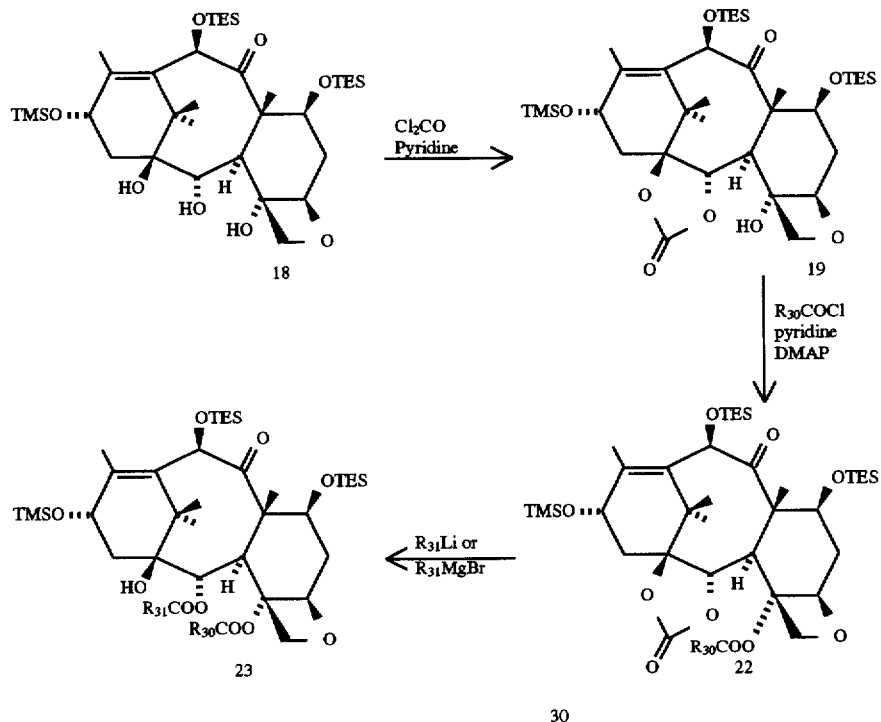

Alternatively, baccatin III may be used as a starting material and reacted as shown in Reaction Scheme 10. After being protected at C7 and C13, baccatin III is reduced with LAH to produce 1,2,4,10 tetraol 24. Tetraol 24 is converted to carbonate 25 using Cl$_2$CO and pyridine, and carbonate 25 is acylated at C10 with an acid chloride and pyridine to produce carbonate 26 (as shown) or with acetic anhydride and pyridine (not shown). Acetylation of carbonate 26 under vigorous standard conditions provides carbonate 27 which is then reacted with alkyl lithiums to provide the baccatin III derivatives having new substituents at C2 and C10.

Scheme 10

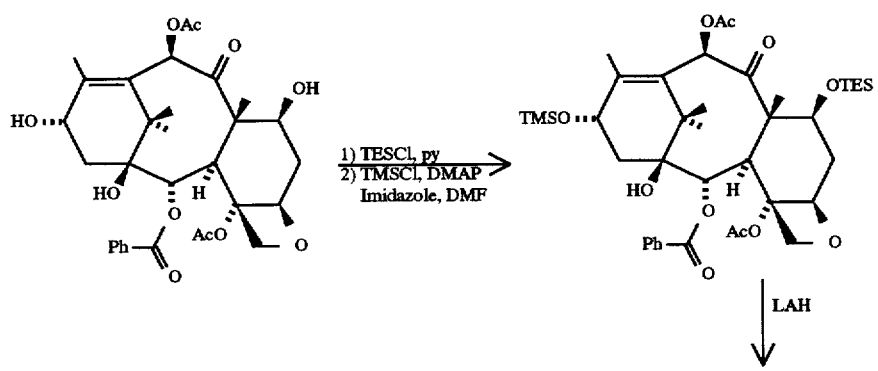

-continued
Scheme 10

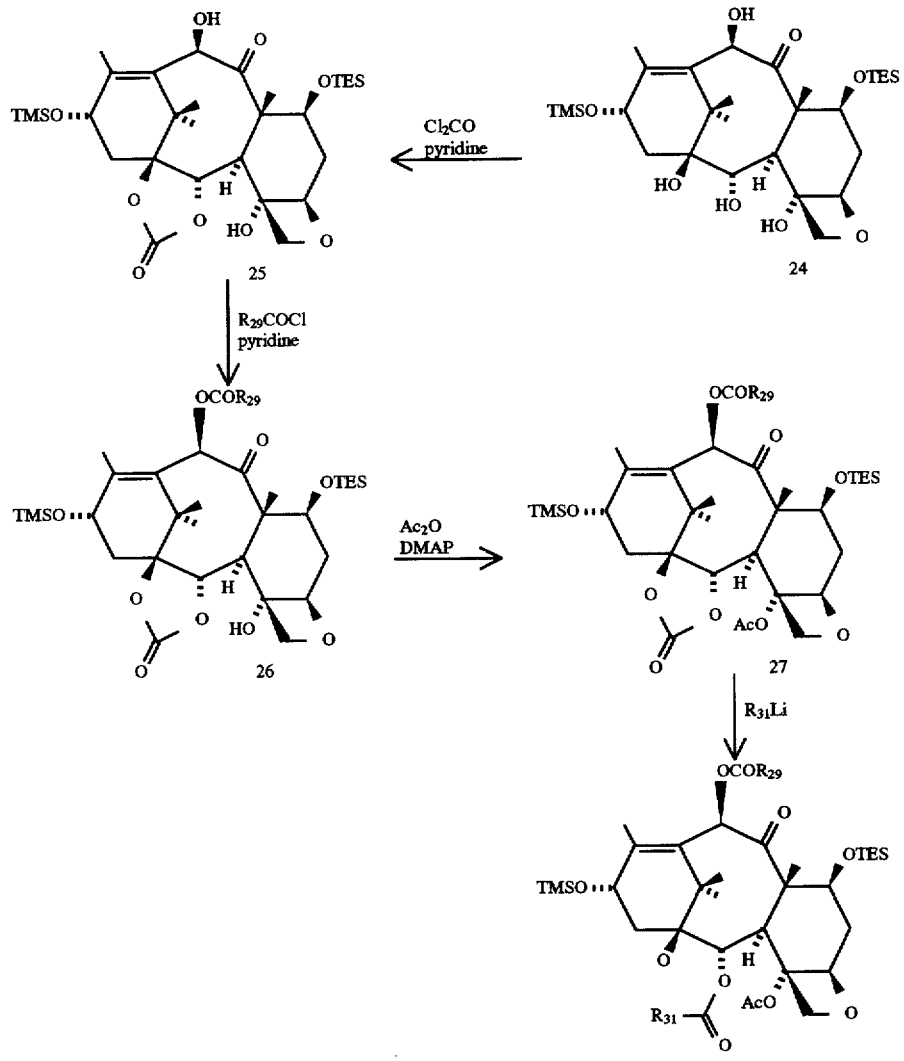

9-desoxo-10-desacetoxy derivatives of baccatin III and 9-desoxo-10-desoxy derivatives of 10-DAB may be prepared by reacting baccatin III or 10-DAB (or their derivatives) with samarium diiodide and thereafter reducing the C9 keto substituent as otherwise described herein. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed.

C7 dihydro and other C7 substituted taxanes can be prepared as set forth in Reaction Schemes 11 and 12.

REACTION SCHEME 11

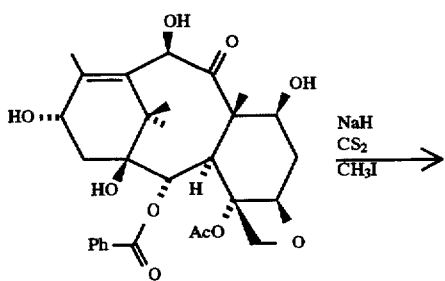

31
-continued
REACTION SCHEME 11

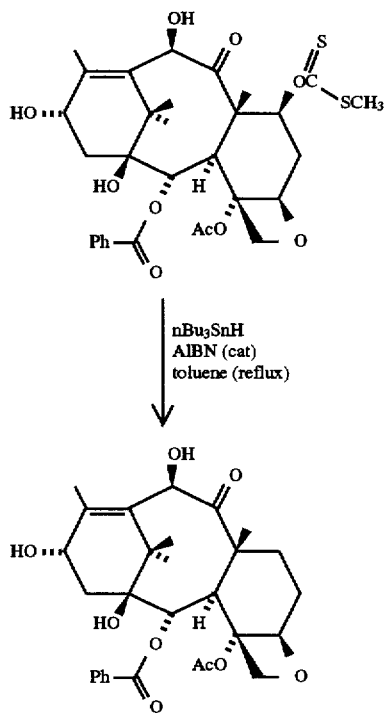

32
-continued
REACTION SCHEME 12

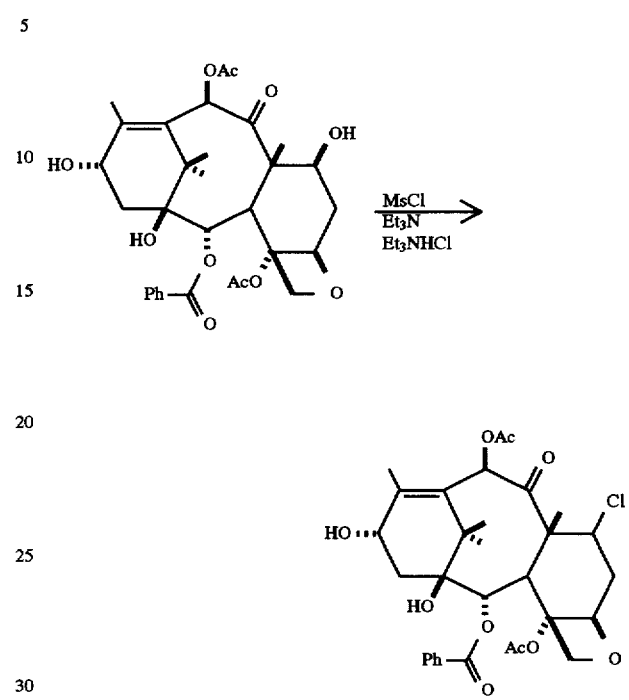

REACTION SCHEME 12

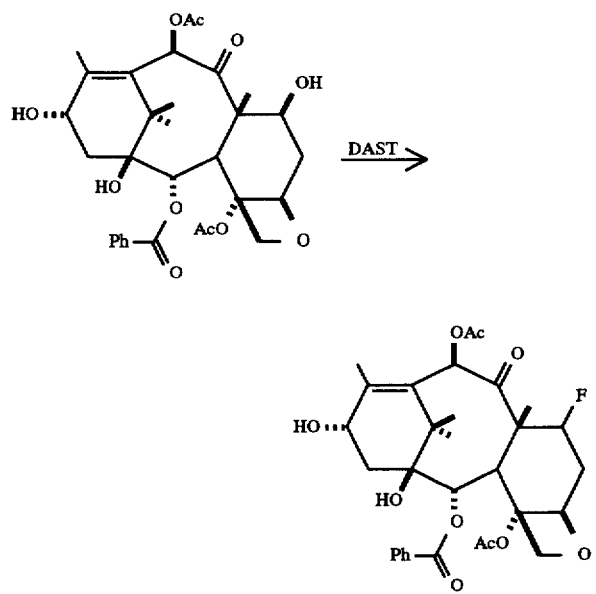

As shown in Reaction Scheme 12, Baccatin III may be converted into 7-fluoro baccatin III by treatment with diethylaminosulfur trifluoride (DAST) at room temperature in THF solution. Other baccatin derivatives with a free C7 hydroxyl group behave similarly. Alternatively, 7-chloro baccatin III can be prepared by treatment of baccatin III with methane sulfonyl chloride and triethylamine in methylene chloride solution containing an excess of triethylamine hydrochloride.

A wide variety of tricyclic taxanes are naturally occurring, and through manipulations analogous to those described herein, an appropriate side chain can be attached to the C13 oxygen of these substances. Alternatively, as shown in Reaction Scheme 13, 7-O-triethylsilyl baccatin III can be converted to a tricyclic taxane through the action of trimethyloxonium tetrafluoroborate in methylene chloride solution. The product diol then reacts with lead tetraacetate to provide the corresponding C4 ketone. This ketone can be reduced to the alcohol with a hydride reducing agent such as sodium borohydride and subsequent acetylation produces the C4, C5 diacetate.

REACTION SCHEME 13

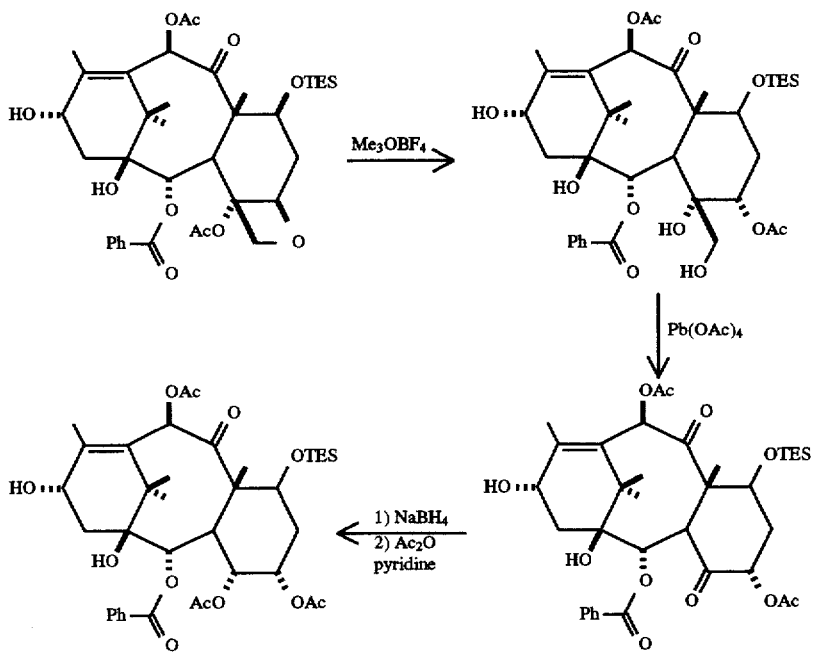

The following examples are provided to more fully illustrate the invention.

EXAMPLE 1

Taxol Using Zinc Alkoxide

To a solution of 7-triethylsilyl baccatin III (100 mg, 0.143 mmol)) in 1 mL of THF at −45° C. was added dropwise 0.286 mL of a 0.5M solution of potassium hexamethyldisilazide in toluene. After 15 min, 32 mg (0.143 mmol) of zinc chloride dimethoxyethane complex was added. After an additional 1 h at −45° C., the mixture was warmed to 0° C. and a solution of (+)-cis-1-benzoyl-3-triethylsilyloxy-4-phenyl-azetidin-2-one (82 mg, 0.215 mmol) in 1 mL of THF was added dropwise to the mixture. The solution was stirred at 0° C. for 3 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by flash chromatography followed by recrystallization to give 139 mg (90%) of (2'R,3'S)-2', 7-(bis)triethylsilyl taxol.

EXAMPLE 2

Taxol Using Cadmium Alkoxide

To a solution of 7-triethylsilyl baccatin III (100 mg, 0.143 mmol)) in 1 mL of THF at −45° C. was added dropwise 0.286 mL of a 0.5M solution of potassium hexamethyldisilazide in toluene. After 15 min, 26 mg (0.143 mmol) of anhydrous cadmium chloride was added. After an additional 1 h at −45° C., the mixture is warmed to 0° C. and a solution of (+)-cis-1-benzoyl-3-triethylsilyloxy-4-phenylazetidin-2-one (82 mg, 0.215 mmol) in 1 mL of THF was added dropwise to the mixture. The solution was stirred at 0° C for 3 h before 1 mL of a 10% solution of AcOH in THF is added. The mixture was partitioned between saturated aqueous NaHCO$_3$ and 60/40 ethyl acetate/hexane. Evaporation of the organic layer gave a residue which was purified by flash chromatography followed by recrystallization to give 131 mg (85%) of (2'R, 3'S)-2', 7-(bis)triethylsilyl taxol.

EXAMPLE 3

Taxol Using Tetrabutylammonium Alkoxide

To a solution of 7-triethylsilyl baccatin III (100 mg, 0.143 mmol)) in 1 mL of THF at −45° C. was added dropwise 0.286 mL of a 0.5M solution of potassium hexamethyldisilazide in toluene. After 15 min, a solution of 16 mg (0.143 mmol) of anhydrous tetramethylammonium chloride in 0.5 mL of THF was added. After an additional 1 h at −45° C., the mixture was warmed to 0° C. and a solution of (+)-cis-1-benzoyl-3-triethylsilyloxy-4-phenylazetidin-2-one (82 mg, 0.215 mmol) in 1 mL of THF was added dropwise to the mixture. The solution was stirred at 0° C. for 3 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by flash chromatography followed by recrystallization to give 134 mg (87%) of (2'R,3'S)-2', 7-(bis)triethylsilyl taxol.

What I claim is:

1. An alkoxide having the formula:

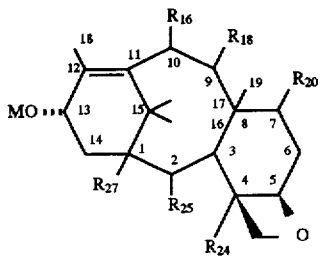

wherein

M comprises ammonium;

$R_{16}$ is hydrogen, —$OCOR_{29}$, hydroxy, or protected hydroxy, or oxo;

$R_{18}$ is hydrogen, hydroxy, protected hydroxy, acyloxy, or oxo;

$R_{20}$ is hydrogen, halogen, protected hydroxy, or —$OR_{28}$;

$R_{24}$ is hydrogen, alkyl, alkenyl, hydroxy, or —$OCOR_{30}$;

$R_{25}$ is hydroxy or —$OCOR_{31}$;

$R_{27}$ is hydrogen, hydroxy, or protected hydroxy;

$R_{28}$ is hydrogen or hydroxy protecting group; and $R_{29}$, $R_{30}$, and $R_{31}$ are independently hydrogen, alkyl, alkenyl, alkynyl, monocyclic aryl or monocyclic heteroaryl.

2. The alkoxide of claim 1 wherein $R_{16}$ is —$OCOR_{29}$ and $R_{29}$ is as defined in claim 1.

3. The alkoxide of claim 1 wherein $R_{18}$ is hydroxy, protected hydroxy or acyloxy.

4. The alkoxide of claim 1 wherein $R_{18}$ is oxo.

5. The alkoxide of claim 1 wherein $R_{25}$ is —$OCOR_{31}$ and $R_{31}$ is as defined in claim 1.

6. The alkoxide of claim 1 wherein $R_{24}$ is hydroxy or —$OCOR_{30}$ and $R_{30}$ is as defined in claim 1.

7. The alkoxide of claim 1 wherein $R_{24}$ is —$OCOR_{30}$, $R_{25}$ is —$OCOR_{31}$, and $R_{30}$ and $R_{31}$ are as defined in claim 1.

8. The alkoxide of claim 1 wherein $R_{20}$ is protected hydroxy or —$OR_{28}$ wherein $R_{28}$ is as defined in claim 1.

9. The alkoxide of claim 1 wherein $R_{24}$ is —$OCOR_{30}$; $R_{25}$ is —$OCOR_{31}$; $R_{27}$ is hydroxy; and $R_{30}$ and $R_{31}$ are as defined in claim 1.

10. The alkoxide of claim 9 wherein R≠is hydroxy, protected hydroxy or —$OCOR_{29}$; and $R_{29}$ is as defined in claim 1.

11. The alkoxide of claim 9 wherein $R_{18}$ is hydrogen, hydroxy, protected hydroxy or acyloxy.

12. An ammonium alkoxide having the formula:

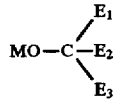

wherein

M comprises ammonium;

$E_1$, $E_2$ and the carbon to which they are attached define a tetracyclic taxane nucleus, and $E_3$ is hydrogen.

13. The ammonium alkoxide of claim 12 wherein M is $C_1$–$C_{10}$ tetralkylammonium.

14. The ammonium alkoxide of claim 12 wherein M is tetramethylammonium or tetrabutylammonium.

15. The alkoxide of claim 1 wherein M is tetramethylammonium or tetrabutylammonium.

16. The alkoxide of claim 1 wherein $R_{16}$ is protected hydroxy or —$OCOR_{29}$, and $R_{29}$ is alkyl;

$R_{18}$ is oxo;

$R_{20}$ is protected hydroxy;

$R_{24}$ is —$OCOR_{30}$ and $R_{30}$ is alkyl;

$R_{25}$ is —$OCOR_{31}$ and $R_{31}$ is aryl; and $R_{27}$ is hydroxy.

17. The alkoxide of claim 16 wherein $R_{16}$ is hydroxy, protected hydroxy or acetoxy;

$R_{18}$ is oxo;

$R_{20}$ is hydroxy or protected hydroxy;

$R_{24}$ is acetoxy;

$R_{25}$ is benzoyloxy; and $R_{27}$ is hydroxy.

18. The alkoxide of claim 16 wherein $R_{16}$ is hydrogen or oxo.

19. The alkoxide of claim 16 wherein $R_{24}$ is —$OCOR_{30}$ and $R_{30}$ is alkyl.

20. The alkoxide of claim 16 wherein $R_{25}$ is —$OCOR_{31}$ and $R_{31}$ is aryl.

21. The alkoxide of claim 16 wherein $R_{24}$ is —$OCOR_{30}$, $R_{25}$ is —$OCOR_{31}$, $R_{30}$ is alkyl, and $R_{31}$ is aryl.

22. The alkoxide of claim 16 wherein M is tetramethylammonium or tetrabutylammonium.

23. The alkoxide of claim 21 wherein $R_{16}$ is protected hydroxy or —$OCOR_{29}$, and $R_{29}$ is alkyl;

$R_{18}$ is oxo;

$R_{20}$ is protected hydroxy;

$R_{24}$ is —$OCOR_{30}$ and $R_{30}$ is alkyl;

$R_{25}$ is —$OCOR_{31}$ and $R_{31}$ is aryl; and $R_{27}$ is hydroxy.

24. The alkoxide of claim 21 wherein $R_{16}$ is hydroxy, protected hydroxy or acetoxy;

$R_{18}$ is oxo;

$R_{20}$ is hydroxy or protected hydroxy;

$R_{24}$ is acetoxy;

$R_{25}$ is benzoyloxy; and $R_{27}$ is hydroxy.

25. The alkoxide of claim 21 wherein $R_{20}$ is hydrogen or protected hydroxy.

26. The alkoxide of claim 21 wherein $R_{18}$ is hydrogen or lower acyloxy.

27. The alkoxide of claim 21 wherein $R_{16}$ is hydrogen or oxo.

28. The alkoxide of claim 21 wherein $R_{24}$ is —$OCOR_{30}$ and $R_{30}$ is alkyl.

29. The alkoxide of claim 21 wherein $R_{25}$ is —$OCOR_{31}$ and $R_{31}$ is aryl.

30. The alkoxide of claim 21 wherein R≧is —$OCOR_{30}$, $R_{25}$ is —$OCOR_{31}$, $R_{30}$ is alkyl and $R_{31}$ is aryl.

* * * * *

UNITED STATES PATENT AND TRADEMARK OFFICE
CERTIFICATE OF CORRECTION

PATENT NO.   : 5,717,115                                    Page 1 of 5
DATED        : February 10, 1998
INVENTOR(S)  : Robert A. Holton It is certified that error appears in the above-identified patent and that said Letters Patent is hereby corrected as shown below:

Title page,
Item [63], Related U.S. Application Data, that portion reading "Ser. No. 863,849, Apr. 19, 1992" should read -- Ser. No. 863,849, Apr. 6, 1992 --.

Column 1,
Lines 43-51, the chemical structure should read:

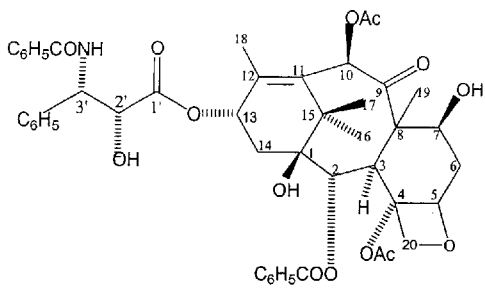

Column 3,
Line 20, "In an effort" should start a new paragraph.

Column 5,
Lines 22-31, the chemical structure should read:

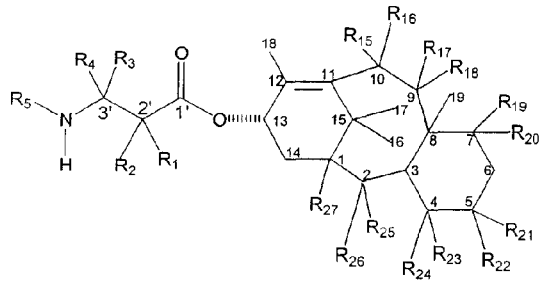

Line 63, "$R_{38}$" should read -- $R_{30}$ --.

UNITED STATES PATENT AND TRADEMARK OFFICE
CERTIFICATE OF CORRECTION

PATENT NO.  : 5,717,115
DATED       : February 10, 1998
INVENTOR(S) : Robert A. Holton It is certified that error appears in the above-identified patent and that said Letters Patent is hereby corrected as shown below:

Column 6,
Lines 14-23, structure (3) should read:

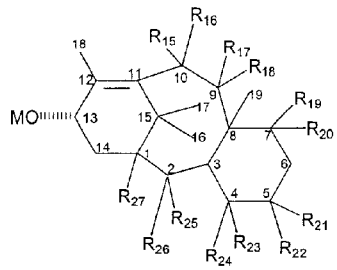

Line 32, ""At"" should read -- "Ar" --.

Column 8,
Line 7, "C1" should read -- Cl --.

Column 10,
Scheme A, that portion reading ←―c―― should read ←――cd――
Scheme B, that portion reading ″″″O̅E̅S should read ″″″OTES Column 11,
Lines 10-27, structure (3) should read:

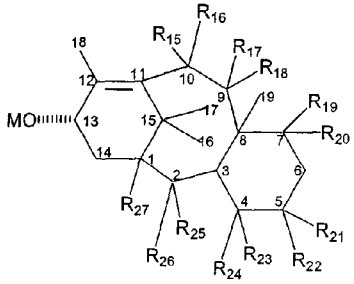

Column 12,
Lines 52-65, the chemical structure (6b) should read:

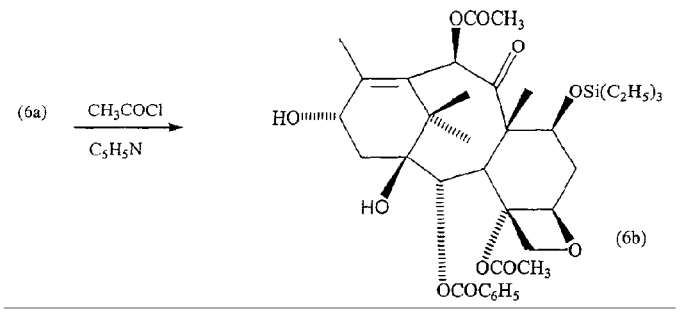

UNITED STATES PATENT AND TRADEMARK OFFICE
CERTIFICATE OF CORRECTION

PATENT NO.    : 5,717,115
DATED         : February 10, 1998
INVENTOR(S)   : Robert A. Holton It is certified that error appears in the above-identified patent and that said Letters Patent is hereby corrected as shown below:

Column 13,
Lines 2-13, the chemical structure (6c) should read:

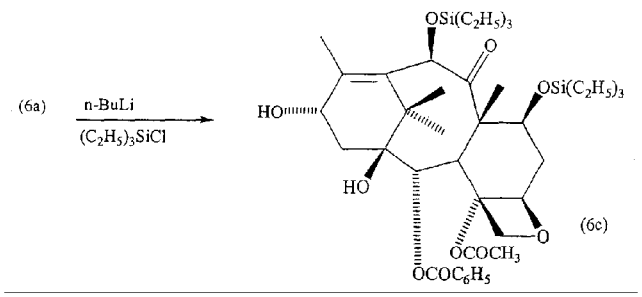

Lines 15-27, the chemical structure (6d) should read:

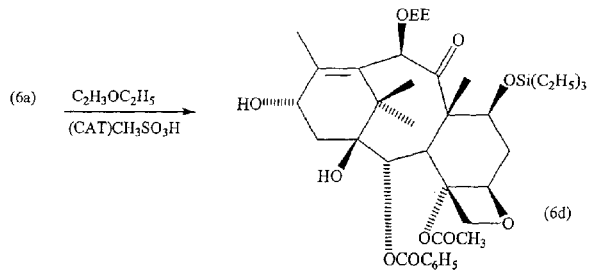

Column 14,
Lines 25-35, chemical structure "7 b-d" should read:

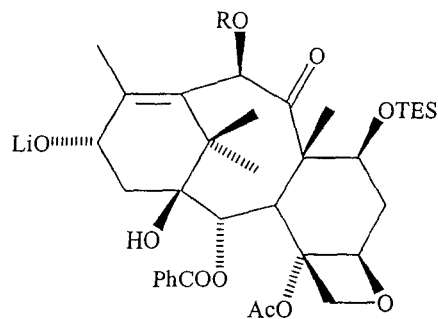

7 b-d

UNITED STATES PATENT AND TRADEMARK OFFICE
CERTIFICATE OF CORRECTION

PATENT NO. : 5,717,115
DATED : February 10, 1998
INVENTOR(S) : Robert A. Holton

It is certified that error appears in the above-identified patent and that said Letters Patent is hereby corrected as shown below:

Column 16,
Line 10, "G is ethylene," should start a new paragraph.
Lines 16 and 39, that portion reading "$X^0$" should read -- $X^\ominus$ --.

Column 17,
Line 24, that portion reading "TESCi" should read -- TESCl --.

Column 18,
Reaction Scheme 2, chemical structure 7, should read:

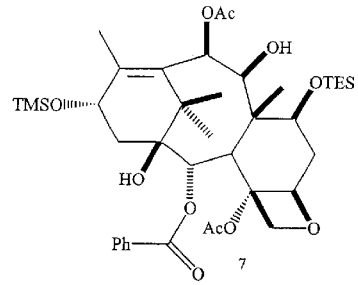

Column 19,
Reaction Scheme 2, chemical structure 9, should read:

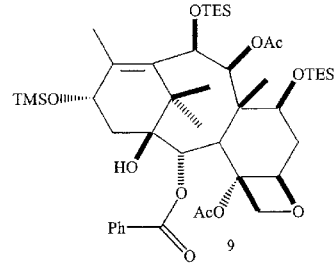

Column 22,
Reaction Scheme 4, chemical structure 14, should read:

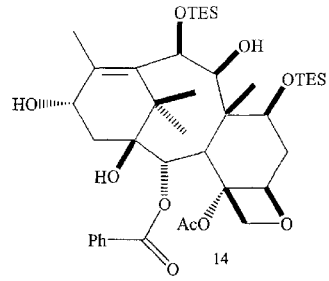

Column 24,
Line 44, "$C^2$" should read -- C2 --.

UNITED STATES PATENT AND TRADEMARK OFFICE
CERTIFICATE OF CORRECTION

PATENT NO. : 5,717,115
DATED : February 10, 1998
INVENTOR(S) : Robert A. Holton

It is certified that error appears in the above-identified patent and that said Letters Patent is hereby corrected as shown below:

Column 25,
Scheme 6, chemical structure 20, should read:

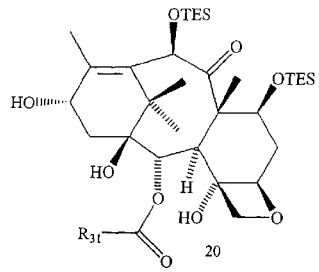

Column 31,
Line 18, that portion reading "AlBN (cat)" should read -- AIBN (cat) --.

Column 35,
Lines 3-12, the chemical structure should read:

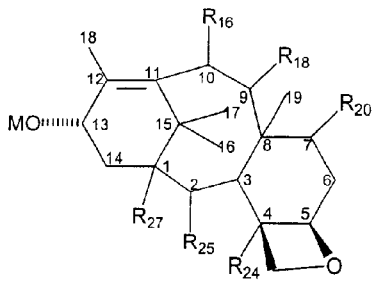

Line 45, "$R_{\neq}$ is" should read -- $R_{16}$ is --.
Lines 53-56, the structure should read:

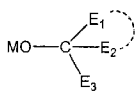

Column 36,
Lines 33, 41, 49, 51, 53, 55, 57 and 59, "claim 21" should read -- claim 22 --.
Line 59, "$R \geqq$ is" should read -- $R_{24}$ is --.

Signed and Sealed this

Sixteenth Day of March, 2004

JON W. DUDAS
*Acting Director of the United States Patent and Trademark Office*